(12) United States Patent
Baguley et al.

(10) Patent No.: US 11,453,662 B2
(45) Date of Patent: Sep. 27, 2022

(54) PROCESS FOR PREPARING MODULATORS OF P300 AND/OR CBP

(71) Applicant: CELLCENTRIC LTD, Cambridge (GB)

(72) Inventors: Paul Baguley, Abingdon (GB); Donald Alan Gilbert, Sudbury (GB); Gareth Harbottle, Nottingham (GB); Colin Lindley, Abingdon (GB); John Paul Madeley, Abingdon (GB); James Vaughan Morey, Sudbury (GB); David Michel Adrien Taddei, Nottingham (GB); Jonathan Trevorrow, Abingdon (GB); David Wood, Sudbury (GB)

(73) Assignee: CELLCENTRIC LTD, Cambridge (GB)

( * ) Notice: Subject to any disclaimer, the term of this patent is extended or adjusted under 35 U.S.C. 154(b) by 116 days.

(21) Appl. No.: 17/047,178

(22) PCT Filed: Apr. 18, 2019

(86) PCT No.: PCT/GB2019/051110
§ 371 (c)(1),
(2) Date: Oct. 13, 2020

(87) PCT Pub. No.: WO2019/202332
PCT Pub. Date: Oct. 24, 2019

(65) Prior Publication Data
US 2021/0163463 A1    Jun. 3, 2021

(30) Foreign Application Priority Data

Apr. 18, 2018  (GB) ..................... 1806320

(51) Int. Cl.
*C07D 413/14*   (2006.01)
(52) U.S. Cl.
CPC ........ *C07D 413/14* (2013.01); *C07B 2200/13* (2013.01)
(58) Field of Classification Search
CPC .................................................. C07D 413/14
See application file for complete search history.

(56) References Cited

U.S. PATENT DOCUMENTS

| 6,498,165 | B1 | 12/2002 | Armstrong et al. |
| 9,095,575 | B2 | 8/2015 | Pikul et al. |

(Continued)

FOREIGN PATENT DOCUMENTS

| EP | 0694535 A1 | 1/1996 |
| EP | 2397471 A1 | 12/2011 |

(Continued)

OTHER PUBLICATIONS

Jones et al., "The Epigenomics of Cancer", Cell, Feb. 23, 2007, vol. 128, pp. 683-692.

(Continued)

*Primary Examiner* — Samira J Jean-Louis
(74) *Attorney, Agent, or Firm* — MH2 Technology Law Group, LLP

(57) ABSTRACT

A process for producing a compound of the following formula (I) which process comprises: (a) treating a compound of the following formula (5) with a compound of the following formula (6) to generate an intermediate compound of the following formula (7); (b) treating a compound of formula (7) as defined above with a compound of the following formula (8); and (c) recovering a compound of formula (I) as defined above. The compound of formula (I) is a promising modulator of p300/CBP activity that has potential utility in treating cancers, including prostate cancer, haematological cancers, bladder cancer and lung cancer.

(Continued)

-continued

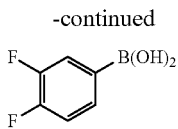

(8)

15 Claims, 2 Drawing Sheets

(56) References Cited

U.S. PATENT DOCUMENTS

| | | | |
|---|---|---|---|
| 10,118,920 | B2 | 11/2018 | Pegg et al. |
| 2010/0179147 | A1 | 7/2010 | Chang et al. |
| 2011/0190343 | A1 | 8/2011 | Gochin et al. |
| 2014/0336190 | A1 | 11/2014 | Aktoudianakis et al. |
| 2016/0184273 | A1 | 6/2016 | Liu et al. |

FOREIGN PATENT DOCUMENTS

| | | | |
|---|---|---|---|
| JP | 2014073982 | A | 4/2014 |
| WO | 02/28839 | A1 | 4/2002 |
| WO | 02/072549 | A1 | 9/2002 |
| WO | 03/072099 | A1 | 9/2003 |
| WO | 2004/063151 | A2 | 7/2004 |
| WO | 2005/021510 | A2 | 3/2005 |
| WO | 2005/118555 | A1 | 12/2005 |
| WO | 2006/124780 | A2 | 11/2006 |
| WO | 2006/136823 | A1 | 12/2006 |
| WO | 2008/009348 | A1 | 1/2008 |
| WO | 2008/070599 | A1 | 6/2008 |
| WO | 2009/000413 | A1 | 12/2008 |
| WO | 2009/023179 | A2 | 2/2009 |
| WO | 2009/079011 | A1 | 6/2009 |
| WO | 2010/068287 | A2 | 6/2010 |
| WO | 2010/075282 | A1 | 7/2010 |
| WO | 2011/045415 | A2 | 4/2011 |
| WO | 2011/097607 | A1 | 8/2011 |
| WO | 2011/143129 | A1 | 11/2011 |
| WO | 2012/036168 | A1 | 3/2012 |
| WO | 2012/107465 | A1 | 8/2012 |
| WO | 2012/116440 | A1 | 9/2012 |
| WO | 2012/133509 | A1 | 10/2012 |
| WO | 2013/130890 | A1 | 9/2013 |
| WO | 2013/186229 | A1 | 12/2013 |
| WO | 2014/012050 | A2 | 1/2014 |
| WO | 2014/054634 | A1 | 4/2014 |
| WO | 2014/078479 | A2 | 5/2014 |
| WO | 2014/157382 | A1 | 10/2014 |
| WO | 2014/182929 | A1 | 11/2014 |
| WO | 2015/023958 | A1 | 2/2015 |
| WO | 2015/086509 | A1 | 6/2015 |
| WO | 2016/016421 | A1 | 2/2016 |
| WO | 2016/086200 | A1 | 6/2016 |
| WO | 2016/170324 | A1 | 10/2016 |
| WO | 2016/200401 | A1 | 12/2016 |
| WO | 2017/024412 | A1 | 2/2017 |
| WO | 2017/059252 | A1 | 4/2017 |
| WO | 2017/100525 | A1 | 6/2017 |
| WO | 2017/106568 | A1 | 6/2017 |
| WO | 2017/223229 | A1 | 12/2017 |
| WO | 2017/223243 | A1 | 12/2017 |
| WO | 2018/073586 | A1 | 4/2018 |
| WO | 2018/097976 | A1 | 5/2018 |

OTHER PUBLICATIONS

Zhong et al., "p300 Acetyltransferase Regulates Androgen Receptor Degradation and PTEN-Deficient Prostate Tumorigenesis", Cancer Research, Mar. 15, 2014, vol. 74, No. 6, pp. 1870-1880.
Cai et al., "Intratumoral De Novo Steroid Synthesis Activates Androgen Receptor in Castration-Resistant Prostate Cancer and Is Upregulated by Treatment with CYP17A1 Inhibitors", Cancer Research, Oct. 15, 2011, vol. 71, No. 20, pp. 6503-6513.
Ogiwara et al., "Targeting p300 Addiction in CBP-Deficient Cancers Causes Synthetic Lethality by Apoptotic Cell Death due to Abrogation of MYC Expression", Cancer Discovery, Apr. 2016, vol. 6, No. 4, 430-445.
Casey et al., "MYC regulates the antitumor immune response through CD47 and PD-L1", Science, Mar. 10, 2016, vol. 352, 15 pages.
Debes et al., "p300 in Prostate Cancer Proliferation and Progression", Cancer Research, Nov. 15, 2003, vol. 63, pp. 7638-7640.
Linja et al., "Expression of Androgen Receptor Coregulators in Prostate Cancer", Clinical Cancer Research, Feb. 1, 2004, vol. 10, 1032-1040.
Ghosh et al., "Regulatory T Cell Modulation by CBP/EP300 Bromodomain Inhibition", The Journal of Biological Chemistry, Jun. 17, 2016, vol. 291, No. 25, pp. 13014-13027.
Hay et al., "Discovery and Optimization of Small-Molecule Ligands for the CBP/p300 Bromodomains", J. Am. Chem. Soc., 2014, vol. 136, pp. 9308-9319 with Supporting Information (S1-S99).
International Search Report and Written Opinion dated Nov. 27, 2017 for International Application No. PCT/GB2017/053152, 8 pages.
International Search Report dated Jun. 17, 2019 for International Application No. PCT/GB2019/051110, 3 pages.
Ley et. al., "Modern Synthetic Methods for Copper-Mediated C(aryl)-O, C(aryl)-N, and C(aryl)-S Bond Formation", Angew. Chern., Int. Edn, 2003, vol. 42, pp. 5400-5449.
Lasko et al., "Discovery of a selective catalytic p300/CBP inhibitor that targets lineage-specific tumours", Nature, 2017, vol. 550, No. 7674, pp. 128-132.

PROCESS FOR PREPARING MODULATORS OF P300 AND/OR CBP

CROSS-REFERENCE TO RELATED APPLICATIONS

This application is a U.S. National Stage application of PCT/GB2019/051110, filed 18 Apr. 2019, which claims priority to GB Application No. 1806320.6, filed 18 Apr. 2018, the entire disclosures of which are hereby incorporated by reference in their entireties.

FIELD OF THE INVENTION

The present invention relates to the preparation of a benzimidazole compound which has utility as a modulator of p300 and/or CBP activity and is therefore potentially useful as a drug substance.

BACKGROUND OF THE INVENTION

Pharmaceutical compounds which are taken to the stage of clinical trials, and which may therefore end up being marketed in licensed medicines, need to be obtainable at high quality on a viable commercial scale, with maximum cost-efficiency. When a promising drug candidate is found, therefore, it is often necessary to reconsider its synthesis: a synthetic route that was suitable on a medicinal chemistry laboratory scale may not lend itself to commercial scaling-up in a way that is reliable and cost-effective.

The compound (S)-6-(5-(3,5-dimethylisoxazol-4-yl)-1-((1R,4S)-4-methoxycyclohexyl)-1H-benzo[d]imidazol-2-yl)-1-(3,4-difluorophenyl)piperidin-2-one, referred to hereafter as compound (I), or a compound of formula (I), is a promising modulator of p300/CBP activity that has potential utility in treating cancers, including prostate cancer, haematological cancers, bladder cancer and lung cancer. On a laboratory scale the compound may be synthesised according to the following scheme A:

SCHEME A

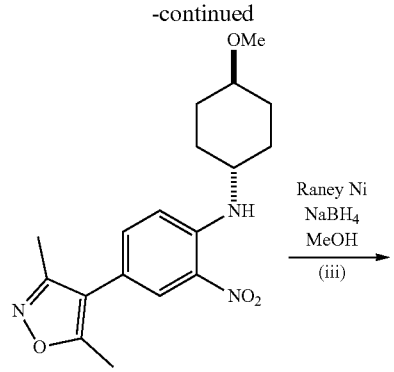
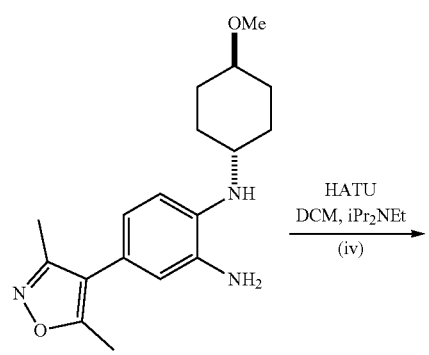
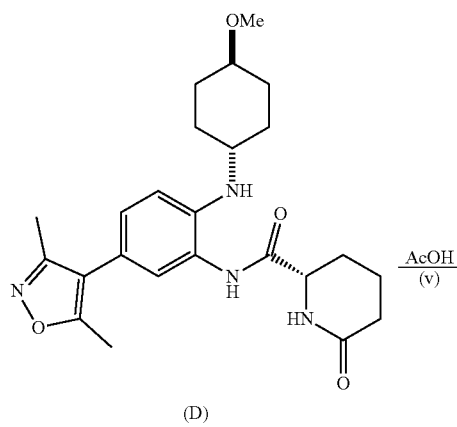
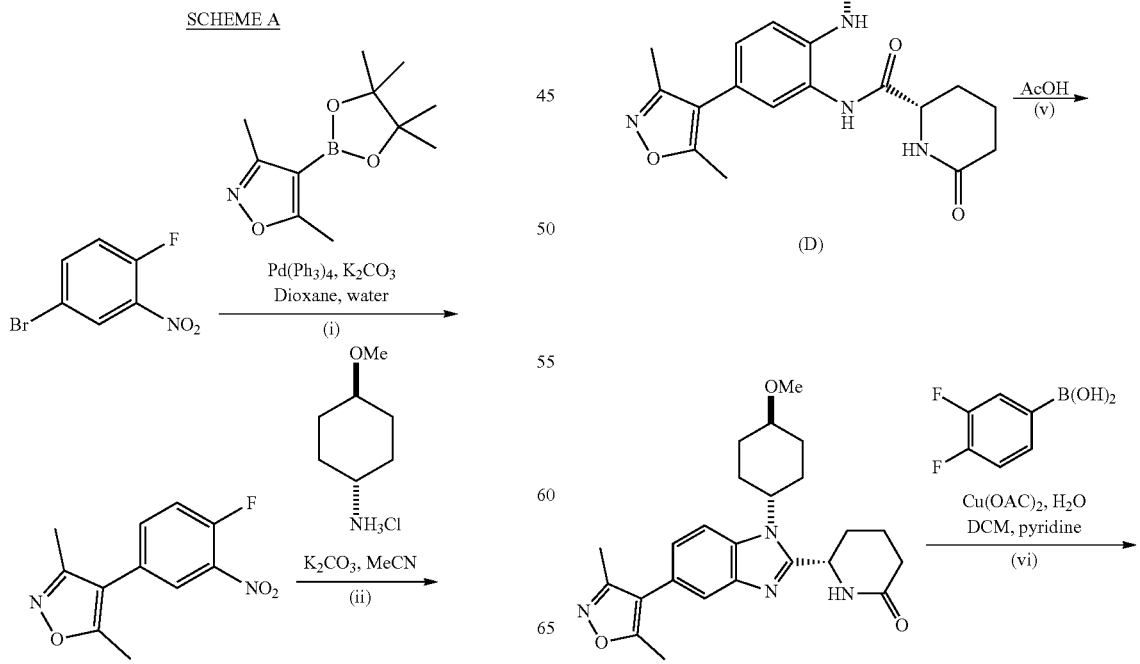
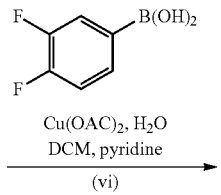

-continued

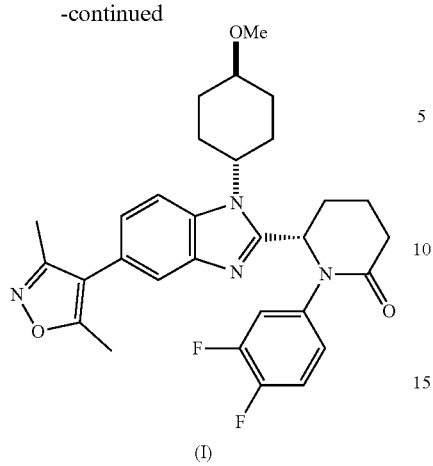

Although successful in the laboratory, scheme A is not well-suited to operation on a commercial scale. There are several reasons for this. A key factor is that the expensive 3,5-dimethylisoxazole-4-boronate ester reagent (3,5-dimethyl-4-(4,4,5,5-tetramethyl-1,3,2-dioxaborolan-2-yl)isoxazole), which gives rise to the left-hand dimethylisoxazole moiety in compound (I), is introduced in step (i). Step (i) is the first of six steps. The left-hand dimethylisoxazole moiety is therefore in place throughout five subsequent transformations. As a result of losses that occur naturally during those transformations, due to varying yields at each stage, the amount of boronate ester starting reagent required to deliver a given quantity of final compound (I) is undesirably high. Another factor is that the use of the HATU reagent (O-(7-azabenzotriazol-1-yl)-N,N,N,N-tetramethyl uronium hexafluorophosphate) in step (iv) necessitates a chromatography step to separate the desired product (D) and causes undesirable etching of glassware.

Factors such as those mentioned above reduce significantly the economic viability of operating scheme A on a commercial scale. There is therefore a need for an alternative process for producing the compound of formula (I) which lends itself better to commercial scale-up.

SUMMARY OF THE INVENTION

The present invention provides a process for producing a compound of the following formula (I):

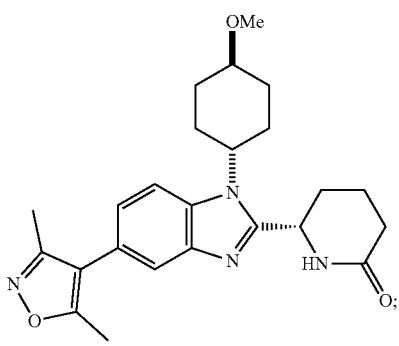

which process comprises:
(a) treating a compound of the following formula (5):

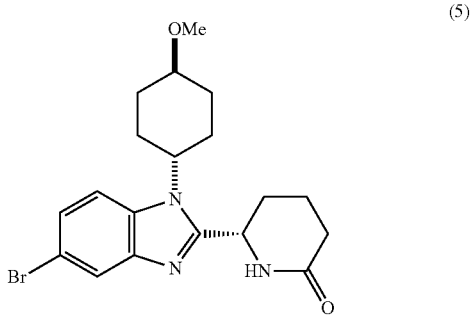

with a compound of the following formula (6):

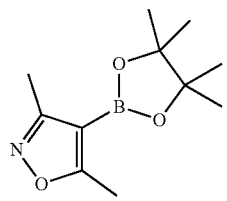

to generate an intermediate compound of the following formula (7):

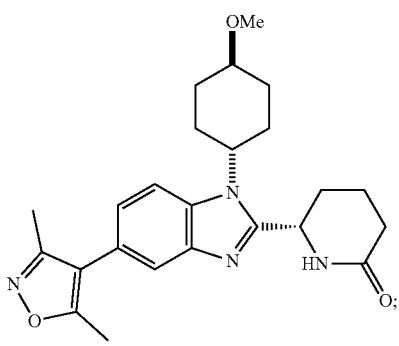

(b) treating a compound of formula (7) as defined above with a compound of the following formula (8):

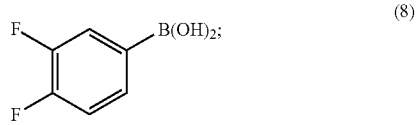 [SMILES: OB(O)c1ccc(F)c(F)c1]

and
(c) recovering a compound of formula (I) as defined above.

The resulting compound of formula (I) may be recrystallized, for instance using ethyl acetate:n-heptane. A thermodynamically stable crystal form may be recovered by this means.

In the above process the 3,5-dimethylisoxazole-4-boronate ester reagent is added to a compound in which the benzimidazole ring, the methoxycyclohexyl group and the right-hand δ-lactam ring are all in place already. Once the 3,5-dimethylisoxazole moiety has been introduced, therefore, only one further process step is needed. As a result, a much smaller amount of 3,5-dimethylisoxazole-4-boronate ester reagent is required to produce a given quantity of compound (I) than in the process of scheme A above.

The compound of formula (I) has biological activity and may thus be useful as a drug substance. A compound produced by the process of the invention as defined above may therefore be formulated with one or more pharmaceutically acceptable carriers or diluents to produce a pharmaceutical composition

DETAILED DESCRIPTION OF THE INVENTION

Figure 1:
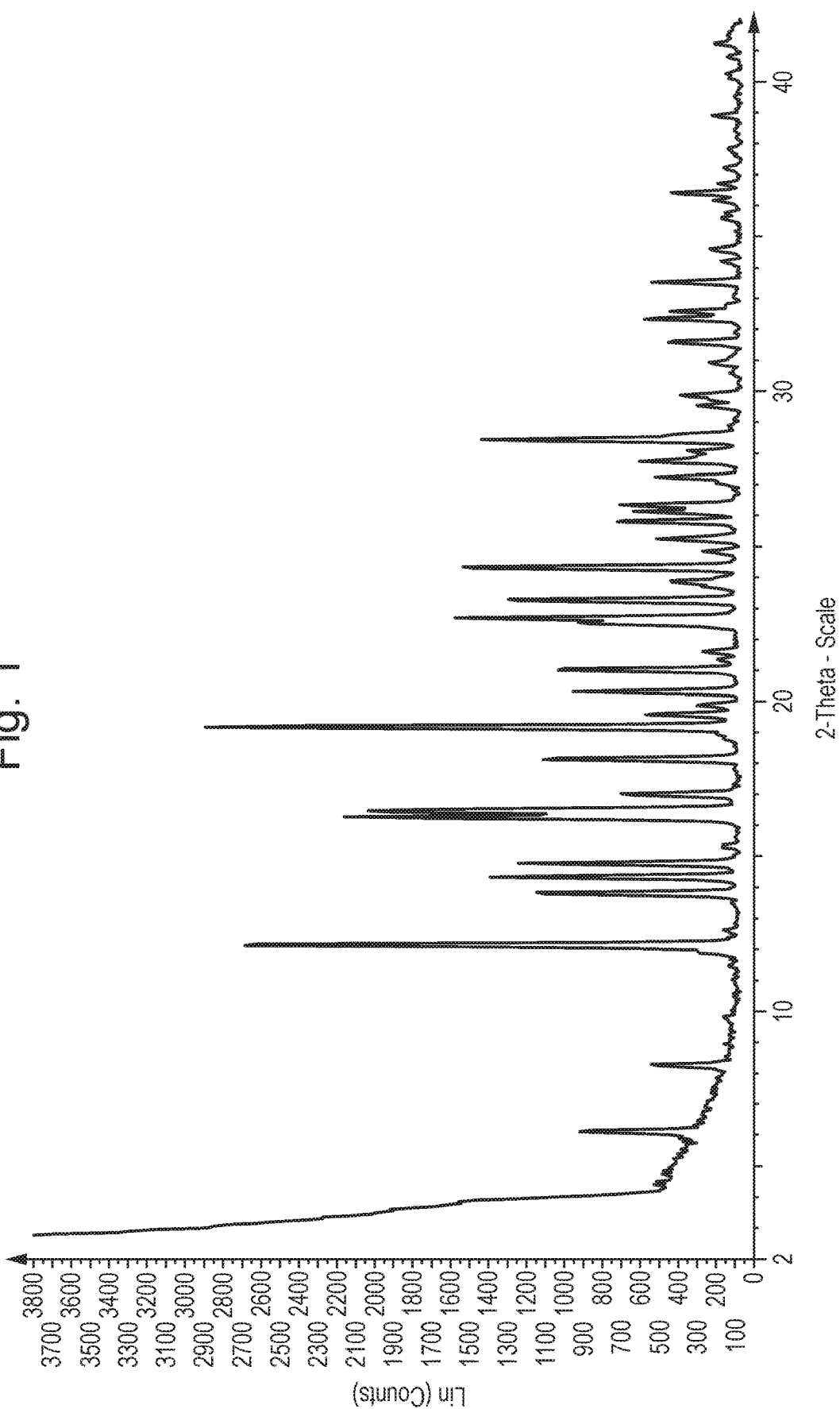
FIG. 1 shows the XRPD diffractogram for crystalline polymorph "Form 1" of the compound of formula (I), obtained as described in Example 5 below.

In the process of the invention as defined above, step (a) is typically conducted in the presence of tetrakis(triphenylphosphine)palladium and a base, in an aprotic solvent and water. The base may be, for instance potassium carbonate. The aprotic solvent is typically 1,4-dioxane.

The compound of formula (7) produced in step (a) may be purified and recrystallized before being treated in step (b) with the compound of formula (8). In one aspect of the invention the process therefore comprises, prior to step (b), purifying and recrystallizing the intermediate compound of formula (7). The compound of formula (7) may be purified by any suitable means, for instance by passage through a silica plug or by treatment with a suitable sequestering agent. When the impurity to be removed comprises boron residues, a suitable sequestering agent is diethanolamine. Recrystallisation of a compound of formula (7) is carried out using a suitable solvent. Suitable solvents include ethyl acetate.

Step (b) of the process of the invention is typically conducted in a polar solvent in the presence of pyridine and $Cu(OAc)_2.H_2O$. During the reaction air, typically filtered air, may be passed over the reaction mixture. The reaction mixture is typically stirred while the air is passed over it. The solvent is typically dichloromethane (DCM).

The compound of formula (I) recovered in step (c) of the process of the present invention shows polymorphism, since it can crystallise in different crystal forms. The crystal form typically produced in the process of the present invention is the thermodynamically most stable form, known as polymorph Form 1. The X-ray data shown in FIGS. 1 and 2 characterise Form 1. However, a metastable crystal form could be obtained instead.

The particular polymorph/crystal form produced is determined by various factors including the choice of solvent used for the recrystallization of the compound of formula (I). Other relevant factors are (a) the amount and rate of stirring/agitation of the solution during crystallisation, and (b) seeding the solution during crystallisation with one or more single crystals of the desired form. The formation of polymorph Form 1 is favoured by the use of a recrystallization solvent selected from butyl acetate, isopropyl acetate, ethyl acetate, ethyl acetate:n-heptane and ethyl acetate:hexane. Other solvents that may give rise to Form 1 include DMSO, dimethoxyethane and acetone:water (5%). Polymorph Form 1 is typically recovered from a suspension/solution of the compound of formula (I) in the relevant solvent by slow cooling. For instance, cooling may take place from 25° C. to 5° C. at 0.1° C./min followed by holding at 5° C. for a period of hours, such as 15-20 hours, for example 16 hours.

The starting compound of formula (5) used in step (a) of the process of the present invention may be prepared by treating a compound of the following formula (4):

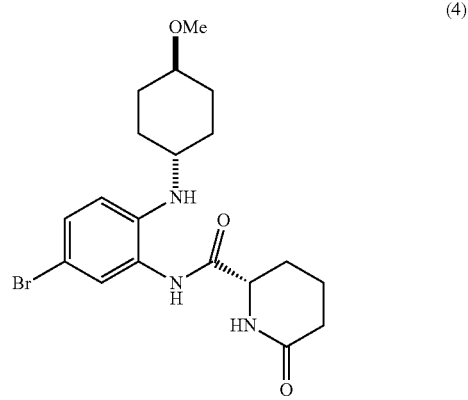

with acetic acid.

The acetic acid promotes cyclisation to form the "imidazole" part of the benzimidazole ring system. In the previous process of scheme A above, this acetic acid-mediated cyclisation was generally performed at a temperature of around 80° C. for a period of several hours. In the process of the invention the reaction is more typically performed at a lower temperature, for instance in the range of 35°-55° C., for instance 40°-50° C. for a period of up to five days. These gentler conditions tend to favour the retention of chiral integrity during the cyclisation step.

The compound of formula (4) shown above may be generated by treating a compound of the following formula (3)

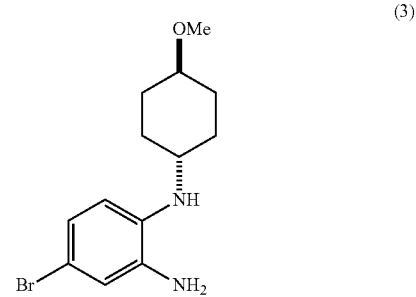

with a compound of the following formula (9):

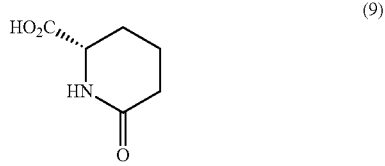

and 1-propylphosphonic acid cyclic anhydride (T₃P®) in a polar organic solvent, in the presence of N,N-diisopropylethylamine. Typically the solvent is dichloromethane.

The replacement of the HATU reagent used for amide coupling in scheme A above by T₃P® in the process of the present invention avoids the need for chromatographic separation of the compound of formula (4). The compound can instead be separated by concentrating. Accordingly, the compound of formula (4) is typically not isolated before undergoing acetic acid-mediated cyclisation to the compound of formula (5).

A compound of formula (3) may be produced by reducing a compound of the following formula (2):

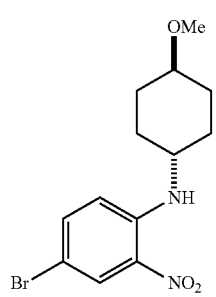

The reduction is performed by any suitable means, for instance by treatment of the compound of formula (2) with $Na_2S_2O_4$ and a base in a polar solvent and water. The base is typically ammonium hydroxide. The polar solvent may be a polar aprotic solvent, for instance THF. The reduction may alternatively be performed using $NaBH_4$ with Raney nickel in MeOH, or by catalytic hydrogenation with Raney nickel.

A compound of formula (2) may be prepared by treating a compound of the following formula (10):

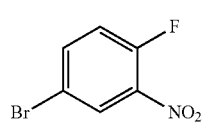

with the following compound:

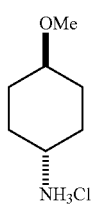

in a polar solvent in the presence of a base. The polar solvent may be a polar aprotic solvent such as acetonitrile. The base may be, for instance, potassium carbonate.

One embodiment of the combination of individual process steps of the present invention, as described above, is shown in the following scheme B:

SCHEME B

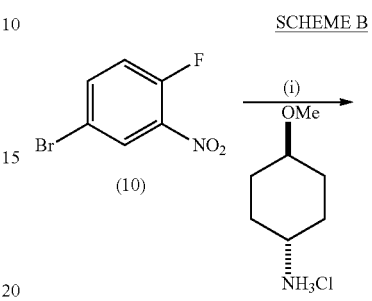

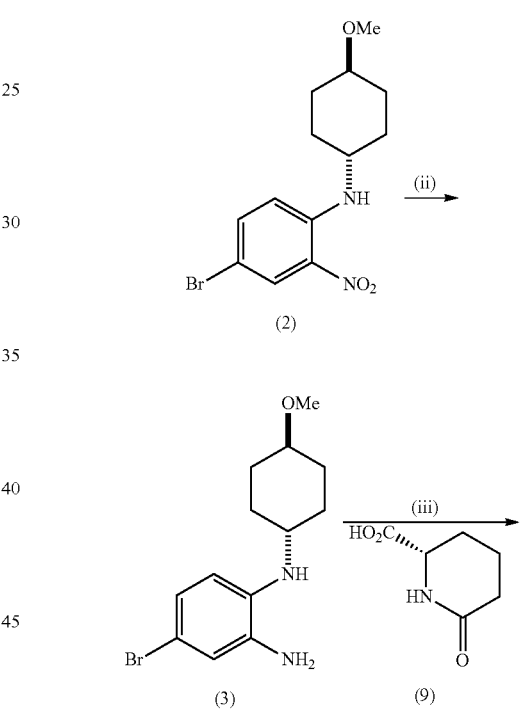

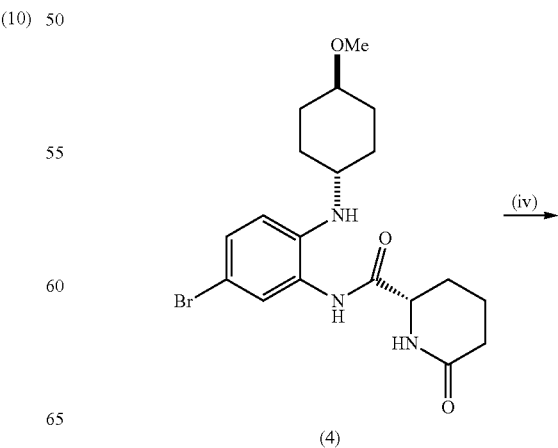

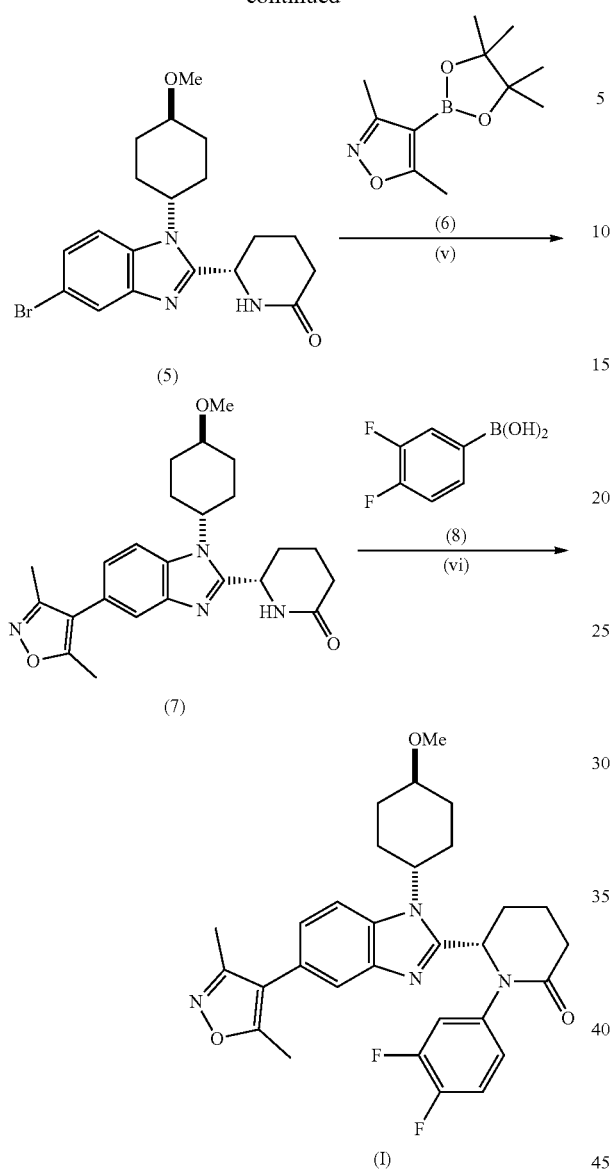

(i) K₂CO₃, MeCN
(ii) Na₂S₂O₄, NH₄OH, THF, H₂O
(iii) 1-propylphosphonic acid cyclic anhydride (T₃P®), dichloromethane, N,N-diisopropylethylamine
(iv) AcOH, 40-50° C.
(v) Pd(Ph₃)₄, K₂CO₃, dioxane, water
(vi) Cu(OAc)₂·H₂O, dichloromethane, pyridine.

It is to be understood that any atom present in the final compound of formula (I), or in any intermediate or starting compound, may be present in any available naturally-occurring isotopic form. For instance, a carbon atom may be $^{12}C$ or $^{13}C$. A hydrogen atom may be $^{1}H$ or $^{2}H$ (deuterium). The compound of formula (I) may thus be prepared in deuterated form, with one or more hydrogen atoms present as $^{2}H$. Any hydrogen atoms or combination thereof may be present as deuterium.

In one embodiment the compound of formula (I) is tri-deuterated, with three $^{2}H$ atoms present in the methoxy group bound to the cyclohexyl substituent. This tri-deuterated compound has the following structural formula (I'):

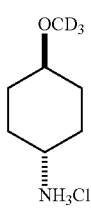

The compound of formula (I') may be prepared by replacing the reagent used in the first step (i) of scheme B above by the following deuterated analogue:

A deuterated compound, such as a compound of the above formula (I'), can be used as a bioanalytical reference standard. It may also have greater stability in the body than the non-deuterated analogue, due to the deuterium isotope effect. It may thus be a useful replacement for the non-deuterated compound in a medical context. A deuterated compound such as the above compound (I') may therefore be used in any treatment method for which the compound of formula (I) is useful. Accordingly, all references below to a compound of formula (I) should therefore be understood to include a reference to the deuterated analogue of formula (I').

A compound of formula (I) produced by the process of the invention has activity as a modulator of p300 and/or CBP activity. It may therefore be used to treat cancer, or another clinical condition in which AR is expressed, or in cancers in which there is activation of CBP and/or p300 function. The cancers that can be treated include those which express AR or are otherwise associated with AR, those that harbour loss of function mutations in CBP or p300 and those which have activated CBP and/or p300.

Cancers that may be treated include, but are not restricted to, prostate cancer, breast cancer, bladder cancer, lung cancer, lymphoma and leukaemia. The prostate cancer may be, for instance, castration-resistant prostate cancer (CRPC). The lung cancer may be, for instance, non-small cell lung cancer or small cell lung cancer. A human or animal patient suffering from cancer may thus be treated by a method comprising the administration thereto of a compound of formula (I) produced in accordance with the invention. The condition of the patient may thereby be improved or ameliorated.

A compound of formula (I) may thus be administered to a human or animal patient in conjunction with radiotherapy or another therapeutic agent for the treatment of cancer. Disclosed herein is therefore a combination therapy wherein a compound of formula (I, or a pharmaceutical composition comprising a compound of formula (I), is administered concurrently or sequentially with radiotherapy; or is administered concurrently sequentially or as a combined preparation with another therapeutic agent or agents, for the treatment of cancer.

The or each other therapeutic agent will typically be an agent conventionally used for the type of cancer being treated. Classes of therapeutic agent with which a compound of formula (I) is typically combined for the treatment of prostate cancer include androgen receptor antagonists, for instance Enzalutamide, Apalutamide, and inhibitors of CYP17A1 (17α-hydroxylase/C17,20 lyase), for instance Abiraterone; for the treatment of lung cancer include cytotoxic chemotherapies, for instance cisplatin, carboplatin, Docetaxel; and for the treatment of bladder cancer include cytotoxic chemotherapies, for instance gemcitabine, cisplatin or immune therapies, for instance, bacillus calmette-guérin (BCG) Classes of therapeutic agent with which compound (I) is typically combined for the treatment of haematological cancers include the following:

a. AML
  i. Azacitadine (hypomethylation agent)
  ii. IDH1/2 inhibitors
b. Multiple myeloma
  i. Dexamethasone
  ii. Proteasome inhibitor+dexamethasone
  iii. Immunomodulatory agents+dexamethasone
c. Non Hodgkins lymphoma
  i. Rituximab
  ii. Lenalidomide (Immunomodulatory agent)
  iii. Chemotherapy
  iv. Ibrutinib (BTK inhibitor)

Other classes of agents with which a compound of the invention could be combined with include immune checkpoint inhibitors, for instance pembrolizumab, nivolumab, atezolizumab, ipilumumab; inhibitors of PARP (poly ADP ribose polymerase) such as Olaparib; and inhibitors of CDK4/6 (cyclin-dependant kinase 4 and 6).

The term "combination" as used herein refers to simultaneous, separate or sequential administration. Where the administration is sequential or separate, the delay in administering the second component should not be such as to lose the beneficial effect of the combination.

Also disclosed herein is a product comprising
  (a) a compound of formula (I) as defined above; and
  (b) one or more other therapeutic agent or agents;
for separate, simultaneous or sequential administration in the prophylactic or therapeutic treatment of cancer, for instance the specific types of cancer mentioned above. The other therapeutic agent may be, for instance, an androgen receptor antagonist, an inhibitor of CYP17A1, an inhibitor of PARP or an inhibitor of CDK4/6. More specifically, it may Enzalutamide, Apalutamide, Abiraterone or Olaparib.

A compound of formula (I) can be administered in a variety of dosage forms, for example orally such as in the form of tablets, capsules, sugar- or film-coated tablets, liquid solutions or suspensions or parenterally, for example intramuscularly, intravenously or subcutaneously. The compound may therefore be given by injection or infusion.

The dosage depends on a variety of factors including the age, weight and condition of the patient and the route of administration. Daily dosages can vary within wide limits and are adjusted to the individual requirements in each particular case. Typically, however, the dosage adopted for each route of administration when the compound is administered alone to adult humans is 0.0001 to 50 mg/kg body weight, most commonly in the range of 0.001 to 10 mg/kg body weight, for instance 0.01 to 1 mg/kg body weight. Such a dosage may be given, for example, from 1 to 5 times daily. For intravenous injection a suitable daily dose is from 0.0001 to 1 mg/kg body weight, preferably from 0.0001 to 0.1 mg/kg body weight. A daily dosage can be administered as a single dosage or according to a divided dose schedule.

A compound of formula (I) is formulated for use as a pharmaceutical or veterinary composition also comprising a pharmaceutically or veterinarily acceptable carrier or diluent. The compositions are typically prepared following conventional methods and are administered in a pharmaceutically or veterinarily suitable form. The compound may be administered in any conventional form, for instance as follows:

A) Orally, for example, as tablets, coated tablets, dragees, troches, lozenges, aqueous or oily suspensions, liquid solutions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of sweetening agents, flavouring agents, colouring agents and preserving agents in order to provide pharmaceutically elegant and palatable preparations.

Tablets contain the active ingredient in admixture with non-toxic pharmaceutically acceptable excipients which are suitable for the manufacture of tablets. These excipients may be for example, inert diluents, such as calcium carbonate, sodium carbonate, lactose, dextrose, saccharose, cellulose, corn starch, potato starch, calcium phosphate or sodium phosphate; granulating and disintegrating agents, for example, maize starch, alginic acid, alginates or sodium starch glycolate; binding agents, for example starch, gelatin or acacia; lubricating agents, for example silica, magnesium or calcium stearate, stearic acid or talc; effervescing mixtures; dyestuffs, sweeteners, wetting agents such as lecithin, polysorbates, tocopherol polyethylene glycol succinate (also known as Vitamin E TGPS), polyglycolised glycerides or lauryl sulphate. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed. Such preparations may be manufactured in a known manner, for example by means of mixing, granulating, tableting, sugar coating or film coating processes.

Formulations for oral use may also be presented as hard gelatin or hydroxypropylmethylcellulose capsules wherein the active ingredient is mixed with an inert solid or semi-solid diluent, for example, calcium carbonate, calcium phosphate, tocopherol polyethylene glycol succinate (Vitamin E TGPS), polyglycolised glycerides or kaolin, or as soft gelatin capsules wherein the active ingredient is present as such, or mixed with water or an oil medium, for example, peanut oil, liquid paraffin, or olive oil.

Aqueous suspensions contain the active materials in admixture with excipients suitable for the manufacture of aqueous suspensions. Such excipients are suspending agents, for example, sodium carboxymethylcellulose, methylcellulose, hydroxypropylmethyl-cellulose, sodium alginate, polyvinylpyrrolidone gum tragacanth and gum acacia; dispersing or wetting agents may be naturally-occurring phosphatides, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides for example polyoxyethylene sorbitan monooleate.

The said aqueous suspensions may also contain one or more preservatives, for example, ethyl or n-propyl p-hydroxybenzoate, one or more colouring agents, such as sucrose or saccharin.

Oily suspension may be formulated by suspending the active ingredient in a vegetable oil, for example *arachis* oil, olive oil, sesame oil or coconut oil, or in a mineral oil such as liquid paraffin. The oily suspensions may contain a thickening agent, for example beeswax, hard paraffin or cetyl alcohol.

Sweetening agents, such as those set forth above, and flavouring agents may be added to provide a palatable oral preparation. These compositions may be preserved by this addition of an antioxidant such as ascorbic acid. Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions may also be in the form of oil-in-water emulsions. The oily phase may be a vegetable oil, for example olive oil or *arachis* oils, or a mineral oil, for example liquid paraffin or mixtures of these. Suitable emulsifying agents may be naturally-occurring gums, for example gum acacia or gum tragacanth, naturally occurring phosphatides, for example soy bean lecithin, and esters or partial esters derived from fatty acids an hexitol anhydrides, for example sorbitan mono-oleate, and condensation products of the said partial esters with ethylene oxide, for example polyoxyethylene sorbitan monooleate. The emulsion may also contain sweetening and flavouring agents. Syrups and elixirs may be formulated with sweetening agents, for example glycerol, sorbitol or sucrose. In particular a syrup for diabetic patients can contain as carriers only products, for example sorbitol, which do not metabolise to glucose or which only metabolise a very small amount to glucose.

Such formulations may also contain a demulcent, a preservative and flavouring and coloring agents.

B) Parenterally, either subcutaneously, or intravenously, or intramuscularly, or intrasternally, or by infusion techniques, in the form of sterile injectable aqueous or oleaginous suspensions. This suspension may be formulated according to the known art using those suitable dispersing of wetting agents and suspending agents which have been mentioned above. The sterile injectable preparation may also be a sterile injectable solution or suspension in a non-toxic paternally-acceptable diluent or solvent, for example as a solution in 1,3-butane diol.

Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition fatty acids such as oleic acid find use in the preparation of injectables.

C) By inhalation, in the form of aerosols or solutions for nebulizers.

D) Rectally, in the form of suppositories prepared by mixing the drug with a suitable non-irritating excipient which is solid at ordinary temperature but liquid at the rectal temperature and will therefore melt in the rectum to release the drug. Such materials are cocoa butter and poly-ethylene glycols.

E) Topically, in the form of creams, ointments, jellies, collyriums, solutions or suspensions.

The invention will be further described in the Examples which follow:

Example 1: Preparation of Compound (5)

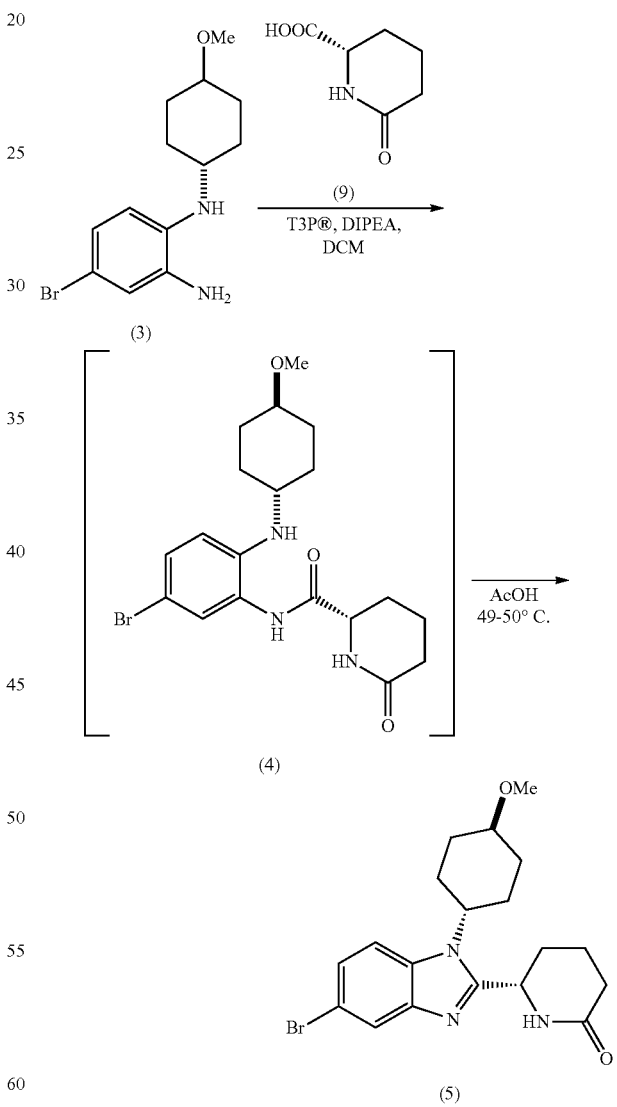

Compound (3) (1002.4 g, 3.35 mol) and Compound (9) (520.7 g, 3.65 mol, 1.04 eq) were dissolved in dichloromethane (6840 mL). N,N-diisopropylethylamine (700 mL) was added slowly, maintaining the temperature at 0 to 5° C., followed by a line rinse with dichloromethane (300 mL).

1-propylphosphonic acid cyclic anhydride, (T3P®, 50% w/w solution in dichloromethane) (3304.8 g, 10.37 mol) was diluted with dichloromethane (1000 mL) and the solution was added to the reaction mixture, maintaining the temperature at 0 to 15° C. Dichloromethane (700 mL) was added as a line rinse. The reaction temperature was adjusted to 15 to 25° C. and the mixture was stirred until the reaction was judged complete (typically, 2 hours).

Aqueous $Na_2CO_3$ solution (0.6M, 10,000 mL) was added, maintaining the temperature at 0 to 25° C. and the phases were separated. The aqueous phase was extracted with dichloromethane (5000 mL) and the combined organic phases were washed with 25% w/w ammonium chloride solution (3×5000 mL). The combined ammonium chloride washes were back-extracted with dichloromethane (5000 mL) and the combined organic extracts were dried over sodium sulphate, filtered and concentrated. The residual solvent was displaced by successive additions of glacial acetic acid followed by concentration, under vacuum, at a temperature not exceeding 50° C.

The residue was dissolved in glacial acetic acid (15,000 mL), warmed to 40-50° C. and stirred at this temperature until the cyclisation to form benzimidazole (5) was judged complete. The mixture was concentrated and the residual solvent was displaced by successive additions of toluene (3×7,500 mL) followed by concentration under vacuum at a temperature not exceeding 50° C., until the acetic acid content was less than 20% w/w. The residue was dissolved in toluene (8,000 mL) and a sample was taken and assayed by NMR at this point.

The contained weight was calculated to be 1240.9 g (91%). δ ($CDCl_3$; 400 MHz): 1.35-1.55, 1.85-2.10, 2.16-2.60 (m, 14H, 7×C$\underline{H}_2$,); 3.34 (m, 1H, C$\underline{H}$OMe); 3.40 (s, 3H, C$\underline{H}_3$O); 4.27 (m, 1H, C$\underline{H}$—N); 4.98 (m, 1H, $\underline{H}$C—NC=O); 6.42 (s, 1H, N—H); 7.12 (d, 1H, Ar—H); 7.57 (d, 1H, Ar—H); 7.63 (s, 1H, Ar—H) ppm.

The toluene solution of Compound (5) was used without further purification.

Example 2: Preparation of Compound (7)

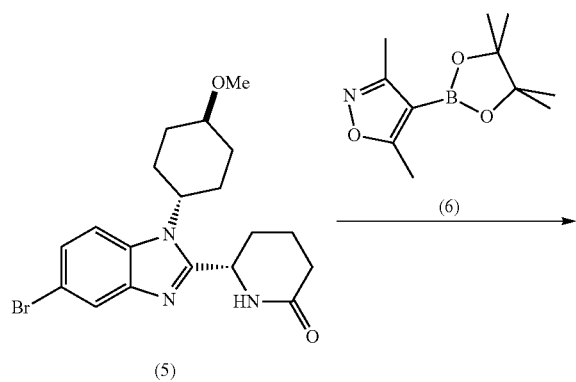

(5)

(6)

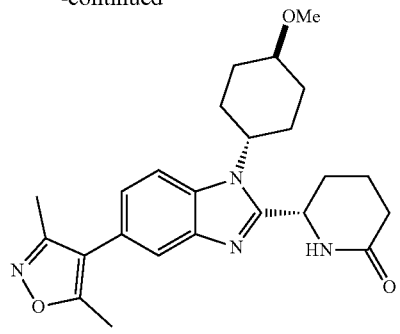

(7)

Reagents: $Pd(P(Ph_3))_4$, $K_2CO_3$, dioxane, water, 85-90° C.

A toluene solution (5807.2 g) containing Compound (5) (818.8 g, 1.94 mol) was concentrated under vacuum at 40-50° C. The remaining solvent was replaced by addition of 1,4-dioxane (4100 mL) and concentrated under vacuum at 40-50° C. The residue was dissolved in 1,4-dioxane (5700 mL) with gentle heating (<30° C.), cooled to 15 to 25° C. and charged to a solution of potassium carbonate anhydrous (1114.6 g, 7.96 mol) in purified water (1640 mL); followed by a line rinse of dioxane (820 mL). 3,5-Dimethyl-4-(4,4,5,5-tetramethyl-1,3,2-dioxaborolan-2-yl)isoxazole (630.7 g, 2.83 mol) was charged and the mixture was sparged with nitrogen for approximately 1 hr 40 minutes, followed by rapid addition of tetrakis(triphenylphosphine)palladium (114.3 g, 0.11 mol). The reaction was heated to 85 to 95° C. and stirred until judged complete (typically 18 hours). After cooling to 15 to 25° C., the reaction was quenched with purified water (11,500 mL) at 15 to 30° C. The mixture was extracted with dichloromethane (3×3,200 mL) dried over sodium sulphate and filtered. The filtrates were concentrated under vacuum (<40° C.) to afford a purple paste, and assayed by $^1$H NMR.

The yield of Compound (7) was estimated to be 800.7 g at this point (94%).

Example 3: Purification and Recrystallization of Compound (7)

Compound (7) (2466.2 g, 5.84 mol) was dissolved in dichloromethane (9865 mL) by rotating on a rotary evaporator using a water bath set at 40 to 45° C. for 10 min. The solution was then cooled to 15 to 25° C. and was poured onto a silica plug (11097.9 g). The desired Compound (7) was eluted from the plug with 5% MeOH/dichloromethane until no further product was observed in the eluent, as determined by TLC by comparison with a 2 mg/mL reference solution; a complete elution was indicated by the final 25000 mL fraction displaying a weaker spot than the reference solution. A total of 150000 mL (60 vol) of 5% MeOH/dichloromethane was required to fully elute the product, Compound (7).

The eluent was evaporated on a rotary evaporator under vacuum with a bath temperature of 40 to 45° C. until dryness. The residue was dissolved in ethyl acetate (12331 mL) and evaporated on a rotary evaporator under vacuum with a bath temperature of 40 to 45° C. until dryness in order to displace residual MeOH/dichloromethane. Ethyl acetate (10840 mL) was added to the residue to give a slurry, which was then heated to 70 to 75° C. and maintained at this temperature for 40 min before being allowed to cool slowly overnight to 15 to 25° C. The product was isolated by filtration, the filter cake was washed twice with ethyl acetate (5000 mL) and then dried on the filter overnight under a nitrogen flow, to give an ethyl acetate content of 0.1% w/w (determined by $^1$H NMR). An off-white solid was produced (2316.0 g, 93.9% th).

δ (CDCl$_3$; 400 MHz): 1.20-1.50, 1.80-2.00, 2.10-2.45 (m, 12H, 6×CH$_2$,); 2.30 (s, 3H, CH$_3$-het); 2.44 (s, 3H, CH$_3$-het); 2.67 (m, 1H, CH(H)—CO); 2.83 (m, 1H, CH(H)—CO); 3.29 (m, 1H, CHOMe); 3.40 (s, 3H, CH$_3$O); 4.04 (m, 1H, CH—N); 5.25 (m, 1H, HC—NC=O); 6.41 (s, 1H, N—H); 7.10 (d, 1H, Ar—H), 7.48 (d, 1H, Ar—H); 7.67 (d, 1H, Ar—H) ppm Example 4: Preparation of Compound (I)

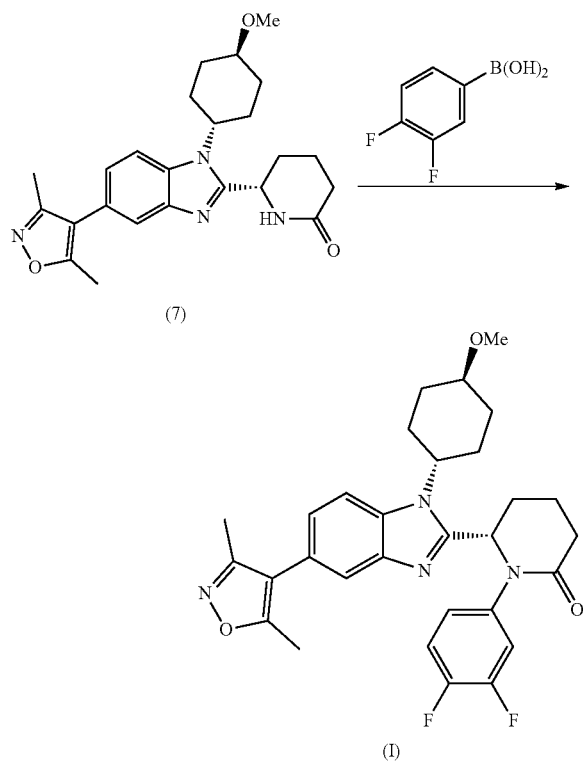

Reagents: Cu(OAc)$_2$·H$_2$O, air, dichloromethane, pyridine

Compound (7) (975.4 g, 2.31 mol) and 3,4-difluorobenzene boronic acid (731.7 g, 4.65 mol) were charged to a suitable reaction vessel, followed by dichloromethane (8800 mL) and the mixture was stirred at 15 to 25° C. for 10 minutes. Pyridine (1800 mL) was added, keeping the temperature below 30° C. (exothermic), followed by dichloromethane (490 mL, line rinse) and finally, Cu(OAc)$_2$.H$_2$O (477.8 g, 1.03 eq.). Filtered air was passed over the reaction mixture, which was stirred at 15 to 25° C. for at least 16 hours, until the reaction was judged complete. The reaction was quenched by addition of purified water (9750 mL) below 30° C. and stirred for 5 minutes. The layers were separated and the aqueous phase was extracted with dichloromethane (4920 mL).

The combined organic extracts were washed with 0.1M Na$_2$EDTA.2H$_2$O solution (2×5000 ml) and 1M hydrochloric acid (4×5000 mL). A check on the pH (target <2) confirmed that all of the pyridine had been removed. The organic layer was then washed with 1.0 M Na$_2$CO$_3$ solution (5020 mL & 5040 mL) and 13% w/v brine (5100 mL) then dried over Na$_2$SO$_4$ and filtered. The organic filtrates were concentrated down to 5 volumes below 45° C., decolourising charcoal (197.6 g) was added and the mixture was stirred for at least 45 minutes at 15 to 25° C. before filtration and concentration. The solvent was replaced with ethyl acetate (5000 mL); added in portions, followed by evaporation. The residue was dissolved in ethyl acetate (2000 mL) and heated to reflux, then n-heptane (3900 mL) was added maintaining a temperature of at least 60° C., during which the product crystallised. The resulting suspension was cooled to 15 to 25° C., over 1 hour and stirred at 15 to 25° C. for 30 minutes. The product was isolated by filtration and the filter cake washed with n-heptane (2×2000 mL). The solid was dried on the filter, under nitrogen, for 4 hours until both the ethyl acetate and n-heptane content was below 1.0% w/w. The yield of Compound (1) was 1073.8 g 87%).

Purification

Crude Compound (1) (2030.5 g) and ethyl acetate (14250 mL) were heated to reflux (75 to 82° C.) and the resulting solution was allowed to cool to 20° C. to 40° C. then filtered hot. A line rise with ethyl acetate (250 mL) followed and the combined filtrates were heated to reflux (75 to 82° C.). After stirring at reflux for 5 minutes, n-heptane (6000 mL) was charged over 30 minutes; maintaining a temperature of at least 60° C., then adjusting to 70° C. Compound (1) seed (20.3 g) was added and the mixture stirred for 5 minutes, then checked to ensure the seed remained undissolved. Further n-heptane (8000 mL) was added over 30 minutes maintaining a temperature of at least 60° C. The mixture was again heated to 70 to 82° C. and stirred for 1 hour. The resulting suspension was allowed to cool to 15 to 25° C. over a period of up to 24 hours. and the product was isolated by filtration.

The filter cake was washed with n-heptane (2×2000 mL) and the solid on the filter was transferred to a vacuum oven and dried under vacuum for 4 hours, until both the ethyl acetate and n-heptane content was below 0.35% w/w.

The weight of Compound (1) obtained was 1822.4 g, (90%)

δ (CDCl$_3$; 400 MHz): 1.25-1.45, 1.88-1.89, 2.21-2.43 (m, 12H, 6×CH$_2$); 2.30 (s, 3H, CH$_3$-het); 2.43 (s, 3H, CH$_3$-het); 2.67 (m, 1H, CH(H)—CO); 2.83 (m, 1H, CH(H)—CO); 3.29 (m, 1H, CHOMe); 3.39 (s, 3H, CH$_3$O); 4.05 (m, 1H, CH—N); 5.26 (m, 1H, HC—NC=O); 6.95-7.05 (m, 4H, Ar—H); 7.48 (d, 1H, Ar—H); 7.67 (m, 1H, Ar—H) ppm Example 5: X-Ray Analysis of Compound (I)

X-Ray Powder Diffraction (XRPD)

An XRPD diffractogram was collected on a Bruker D8 diffractometer using Cu Kα radiation (40 kV, 40 mA) and a 0-2θ goniometer fitted with a Ge monochromator.

The sample was analysed under ambient conditions as a flat plate specimen. The XRPD diffractogram of Form 1 is shown in accompanying FIG. 1.

The details of the standard data collection method were:
Angular range: 2 to 42° 2θ
Step size: 0.05° 2θ
Collection time: 0.5 s/step (total collection time: 6.40 min)

Single Crystal X-Ray Diffraction

Figure 2:
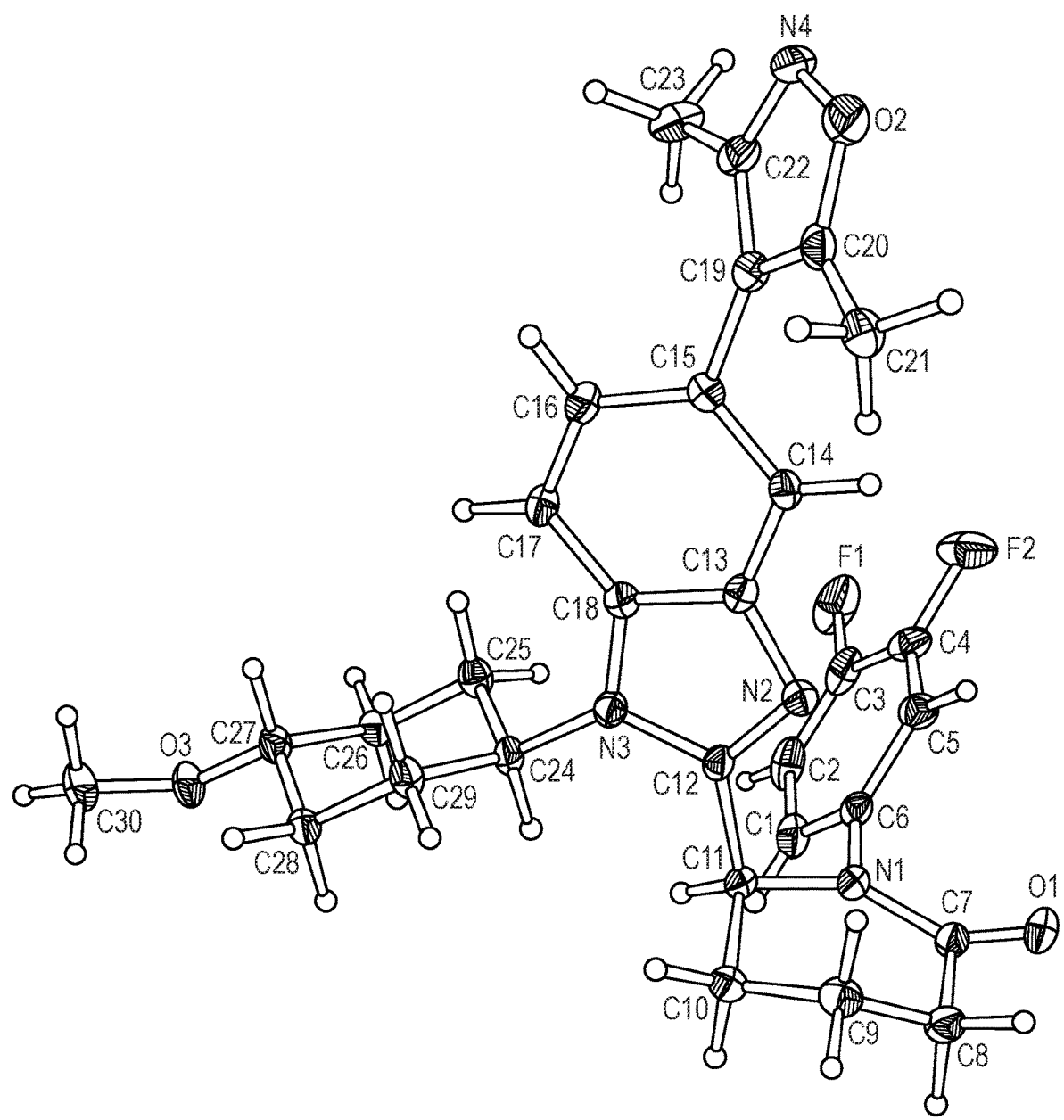
FIG. 2 is an ORTEP (Oak Ridge Thermal Ellipsoid Plot) diagram of the structure of a single crystal of "Form 1" of the compound of formula (I), obtained as described in Example 5 below

A crystal of compound (I) of sufficient size and quality for analysis by single crystal X-ray diffraction was isolated by slow evaporation from a solution of compound (I) in butyl acetate at ambient conditions. An ellipsoid plot (ORTEP diagram) of the structure derived from the single crystal study is shown in FIG. 2.

Example 6: Tablet Composition

Tablets, each weighing 0.15 g and containing 25 mg of compound (I) are manufactured as follows:
Composition for 10,000 tablets
Compound (I) (250 g)
Lactose (800 g)
Corn starch (415 g)
Talc powder (30 g)
Magnesium stearate (5 g)

Compound (I), lactose and half of the corn starch are mixed. The mixture is then forced through a sieve 0.5 mm mesh size. Corn starch (10 g) is suspended in warm water (90 ml). The resulting paste is used to granulate the powder. The granulate is dried and broken up into small fragments on a sieve of 1.4 mm mesh size. The remaining quantity of starch, talc and magnesium is added, carefully mixed and processed into tablets.

Example 7: Capsule Composition

Capsules, each weighing 0.21 g and containing 25 mg of compound (I) are manufactured as follows:
Composition for 10,000 Capsules
Compound (I) (250 g)
Tocopherol polyethylene glycol succinate (1850 g)
10,000 size 3 gelatin capsules Tocopherol polyethylene glycol succinate is melted at a temperature exceeding its melting point (40° C.). Compound (I) and molten tocopherol polyethylene glycol succinate are then mixed to form a homogeneous mixture with no visible lumps or aggregates. The mixture is maintained in a molten state and is filled into size 3 gelatin capsules.

Example 8: Injectable Formulation

| Compound (I) | 200 mg |
| Hydrochloric Acid Solution 0.1M or Sodium Hydroxide Solution 0.1M q.s. | to pH 4.0 to 7.0 |
| Sterile water q.s. to | 10 mL |

Compound (I) is dissolved in most of the water (35°–40° C.) and the pH adjusted to between 4.0 and 7.0 with the hydrochloric acid or the sodium hydroxide as appropriate. The batch is then made up to volume with water and filtered through a sterile micropore filter into a sterile 10 mL amber glass vial (type 1) and sealed with sterile closures and overseals.

Example 9: Intramuscular Injection

| Compound (I) | 200 mg |
| Benzyl Alcohol | 0.10 g |
| Glycofurol 75 | 1.45 g |
| Water for injection q.s to | 3.00 mL |

Compound (I) is dissolved in the glycofurol. The benzyl alcohol is then added and dissolved, and water added to 3 ml. The mixture is then filtered through a sterile micropore filter and sealed in sterile 3 ml glass vials (type 1).

Example 10: Syrup Formulation

| Compound (I) | 250 mg |
| Sorbitol Solution | 1.50 g |
| Glycerol | 2.00 g |
| Sodium benzoate | 0.005 g |
| Flavour | 0.0125 mL |
| Purified Water q.s. to | 5.00 mL |

Compound (I) is dissolved in a mixture of the glycerol and most of the purified water. An aqueous solution of the sodium benzoate is then added to the solution, followed by addition of the sorbitol solution and finally the flavour. The volume is made up with purified water and mixed well.

The invention claimed is:

1. A process for producing a compound of the following formula (I):

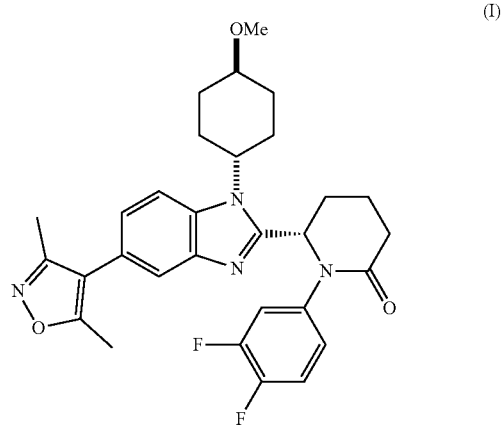

which process comprises:

(a) treating a compound of the following formula (5):

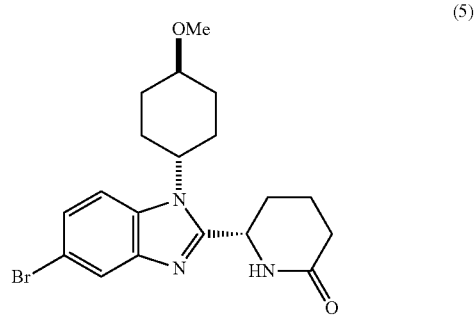 [SMILES: CO[C@H]1CC[C@H](n2c([C@@H]3CCCC(=O)N3)nc3cc(Br)ccc32)CC1]

with a compound of the following formula (6):

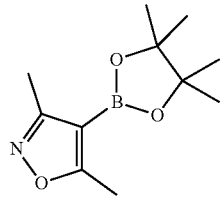
(6)

to generate an intermediate compound of the following formula (7):

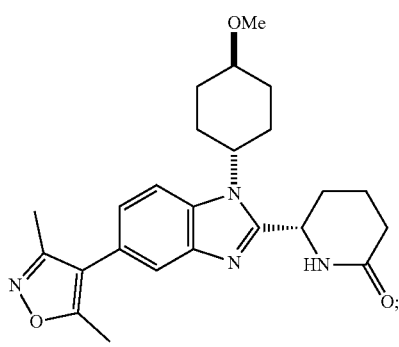
(7)

(b) treating a compound of formula (7) as defined above with a compound of the following formula (8):

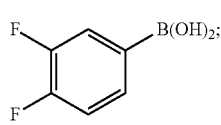
(8)

and (c) recovering a compound of formula (I) as defined above.

2. A process according to claim 1, wherein step (a) is conducted when tetrakis(triphenylphosphine)palladium and potassium carbonate in 1,4-dioxane and water are present.

3. A process according to claim 1, wherein step (b) is conducted in dichloromethane in when pyridine and Cu(OAc)$_2$.H$_2$O are present.

4. A process according to claim 1, which further comprises, prior to step (b), purifying and recrystallizing the intermediate compound of formula (7).

5. A process according to claim 4, wherein the compound of formula (7) is purified by passage through a silica plug.

6. A process according to claim 4, wherein the compound of formula (7) is recrystallized from ethyl acetate.

7. A process according to claim 1, which further comprises producing the compound of formula (5) by treating a compound of the following formula (4):

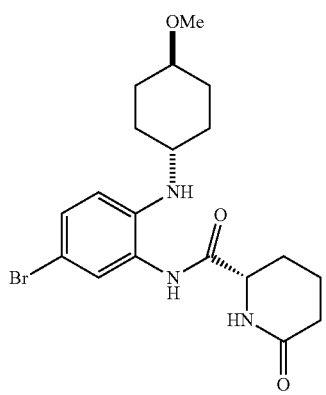
(4)

with acetic acid.

8. A process according to claim 7, wherein the reaction between the compound of formula (4) and acetic acid is conducted at a temperature of from 40°-50° C.

9. A process according to claim 7, wherein the compound of formula (4) is generated by treating a compound of the following formula (3)

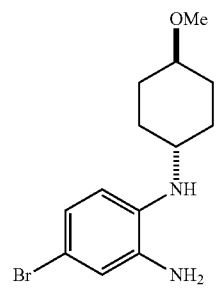
(3)

with a compound of the following formula (9):

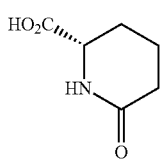
(9)

and 1-propylphosphonic acid cyclic anhydride (T$_3$P®) in dichloromethane, when N,N-diisopropylethylamine is present.

10. A process according to claim 1, which further comprises recrystallizing the compound of formula (I) from ethyl acetate:n-heptane to provide a recrystallized product, and recovering the recrystallized product.

11. A process according to claim 1, which further comprises formulating the resulting compound of formula (I) with one or more pharmaceutically acceptable carriers or diluents to produce a pharmaceutical composition.

12. A compound which is of the following formula (I'):

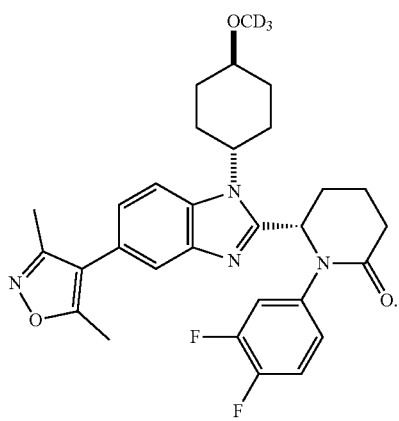

(I')

13. A compound of the following formula (I) in crystal form:

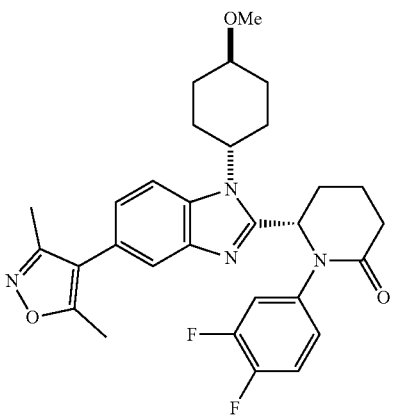

(I)

wherein the crystal form is characterised by data shown in an XRPD diffractogram as shown in FIG. 1 and/or by a single crystal X-ray structure as shown in FIG. 2.

14. A pharmaceutical composition comprising a compound as defined in claim 12 and one or more pharmaceutically acceptable carriers or diluents.

15. A pharmaceutical composition comprising a compound as defined in claim 13 and one or more pharmaceutically acceptable carriers or diluents.

* * * * *